United States Patent [19]

Johnson et al.

[11] Patent Number: 4,990,672
[45] Date of Patent: Feb. 5, 1991

[54] PROPYLENE-LINKED POLYETHYLENE POLYAMINES AND A PROCESS FOR MAKING SAME

[75] Inventors: Thomas A. Johnson, Orefield, Pa.; Ismail O. Abdalmuhdi, Princeton, N.J.

[73] Assignee: Air Products and Chemicals, Inc., Allentown, Pa.

[21] Appl. No.: 359,059

[22] Filed: May 30, 1989

[51] Int. Cl.$^5$ .................... C07C 85/12; C07C 85/20; C07C 209/00
[52] U.S. Cl. .................... 564/490; 544/357; 544/402; 564/491; 564/487
[58] Field of Search ............ 544/357, 402; 564/490, 564/491, 487; 260/690

[56] References Cited

U.S. PATENT DOCUMENTS

| | | | |
|---|---|---|---|
| 3,700,598 | 10/1972 | Plonsker et al. | 564/491 |
| 4,137,267 | 1/1979 | Reid et al. | 260/583 P |
| 4,547,591 | 10/1985 | Brennan et al. | 564/479 |
| 4,552,862 | 11/1985 | Larkin | 502/306 |
| 4,721,811 | 1/1988 | Sherwin et al. | 564/491 |
| 4,845,297 | 7/1989 | Kumoi et al. | 564/490 |

FOREIGN PATENT DOCUMENTS

| | | | |
|---|---|---|---|
| 58-140571 | 8/1983 | Japan . | |
| 2201848 | 9/1987 | Japan | 564/491 |
| 948865 | 2/1964 | United Kingdom | 564/491 |

Primary Examiner—Cecilia Shen
Attorney, Agent, or Firm—Russell L. Brewer; James C. Simmons; William F. Marsh

[57] ABSTRACT

This invention relates to propylene-linked polyethylene polyamines and a process for preparing such propylene-linked polyethylene polyamines. These propylene-linked polyethylene polyamines are characterized as having high molecular weight and the amine value is distributed over a wide range of primary, secondary, and tertiary amine functionality.

The propylene-linked polyethylene polyamines are prepared by reacting a polyamine containing an ethylene amine functionality with acrylonitrile or methacrylonitrile to form a cyanoethylated polyamine containing the ethylene linkage and then reductively alkylating the resulting cyanoethylated derivative in the presence of a polyamine containing an ethylene linkage. Typically, a polyethylene polyamine such as diethylenetriamine or triethylene tetramine is reacted with acrylonitrile and then hydrogenated under reductive alkylation conditions.

7 Claims, No Drawings

PROPYLENE-LINKED POLYETHYLENE POLYAMINES AND A PROCESS FOR MAKING SAME

TECHNICAL FIELD

This invention relates to propylene-linked polyethylene polyamines and to a process for producing the propylene-linked polyethylene polyamines through cyanoethylation of an ethylene radical containing polyamine followed by reductive alkylation.

BACKGROUND OF THE INVENTION

Polyethylene polyamines such as diethylenetriamine, triethylene tetramine, and tetraethylenepentamine as well as amine derivatives of these polyethylene amines are known and have been widely used in the manufacture of lubricating formulations and as epoxy curing agents. The following patents are representative of various polyethylene polyamine:

U.S. Pat. No. 547,591 discloses a process for producing polyethylene polyamines by reacting an ethylene amine with monoethanolamine in the presence of silica-alumina catalyst, preferably one containing an acidic phosphorus cocatalyst. Linear polyethylene polyamine such as diethylene triamine and tetraethylenepentamine are produced. Japanese patent publication SHO 58-140571 discloses a process for producing polyamines by the catalytic reduction of a cyanoethylated N-(2-aminoethyl) piperazine. Other cyanoalkylated amines such as the cyanoalkylated derivatives of polyalkylene polyamines including diethylenetriamine and triethylene tetramine are also suggested.

U.S. Pat. No. 4,137,267 discloses a process for producing alkyl-1,3- diamino propanes by contacting an alkyl amino propionitrile with hydrogen and ammonia in the presence of a hydrogenation catalyst. Typically, a C10 to C20 primary amine is reacted with acrylonitrile or methacrylonitrile in the presence of hydrogen chloride and then catalytically reduced in the presence of hydrogen and ammonia over a hydrogenation catalyst, e.g., platinum, palladium, rhodium, etc.

U.S. Pat. No. 4,552,862 discloses a method for stabilizing pellets of a hydrogenation catalyst during hydrogenation which typically include the hydrogenation of cyanoethylated ethylene containing polyamines. Typically, the polyamine substrate is the cyanoethylated product resulting by the reaction of acrylonitrile with an amine or polyamine which includes piperazine, ethylenediamine, monoethanolamine, diethylenetriamine, and 3-aminopropanol. The catalytic hydrogenation is carried out in the presence of hydrogen and ammonia to prevent trimolecular coupling to produce secondary amines.

SUMMARY OF THE INVENTION

This invention pertains to propylene linked polyamines wherein a polyamine containing an ethylene linkage is reacted with acrylonitrile or metnacrylonitrile and then the cyanoethylated polyamine reductively alkylated with a polyamine containing an ethylene linkage in the presence of hydrogen. These propylene-linked polyamines typically are the reaction product of acrylonitrile or methylacrylonitrile with a polyethylene polyamine and then the resulting cyanoethylated polyethylene polyamine reductively alkylated in the presence of additional polyethylene polyamine.

The propylene-linked polyamines containing the ethylene linkage are characterized in that they are high molecular weight and as a result are relatively nonvolatile as compared to other polyethylene polyamines; they are well suited for producing lubricating formulations and because of their diverse primary, secondary and tertiary amine functionality are well suited as curing agents for epoxy resins. They are further characterized as having a high amine value distributed over the amine chain resulting in high performance vis-a-vis weight.

DETAILED DESCRIPTION OF THE INVENTION

Propylene-linked polyethylene polyamines produced herein are high molecular weight polyethylene polyamines and these are polyethylene polyamines coupled via a propylene or substituted linkage as opposed to high molecular weight oligomers of reformed polyethylene polyamines. These propylene-linked polyethylene polyamines products fall into a number of structural classes. The classes are: (1) predominantly linear polyamines linked by one or more 1,3-propylene groups: (2) predominantly branched polyamines linked by one or more 1,3-propylene groups: (3) cyclic polyamines linked by one or more 1,3-propylene groups and () combinations of linear, branchd and cyclic polyamines linked by one or more 1,3-propylene groups. Further, the linked polyamines may have one or two pendent 3-aminopropyl groups attached or linked to the backbone. The following structures cover the range of compositions described above.

Propylene-linked polyethylene polyamines

A.

and

B.

and

Dipropyleneamino-linked polyethylene polyamines

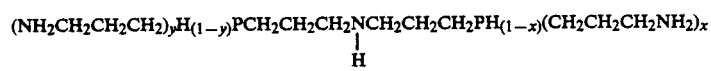

C.

and

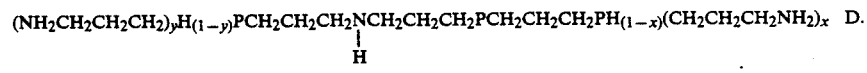

D.

where x and y are 0 or 1; x need not equal y; and where P is a polyamine from the families consisting of Linear Polyamine Radicals, Branched Polyamine Radicals, and Cyclic Polyamine Radicals as represented by the following.

Examples of the Linear Polyamine Radicals family are:

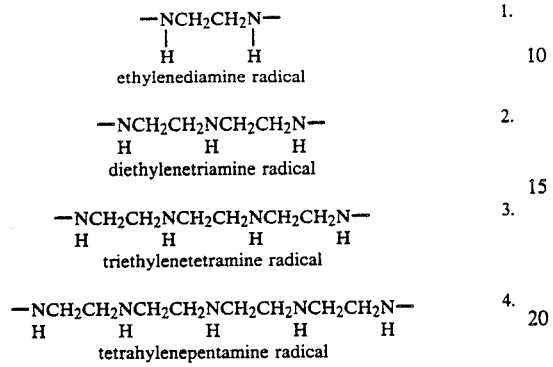

Examples of a branched polyamine radical family are represented as follows:

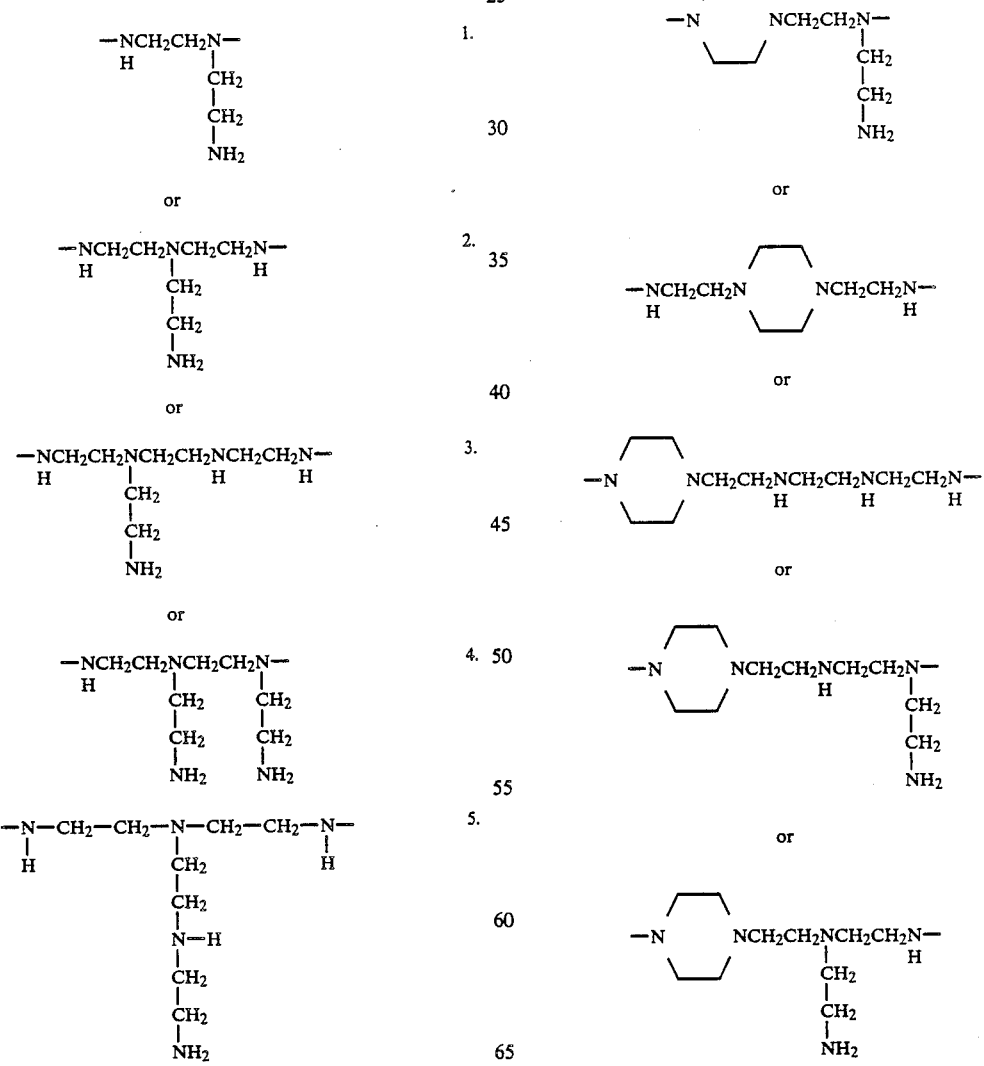

Examples of a cyclic polyamine radical family are represented as follows:

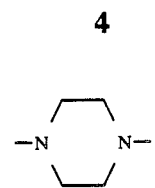

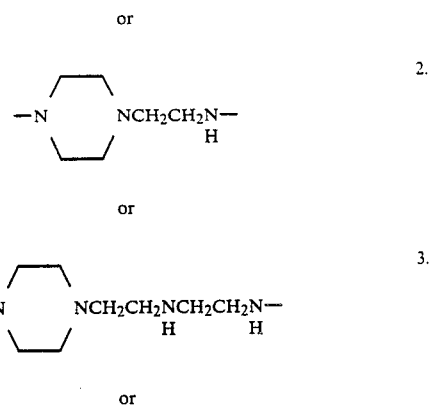

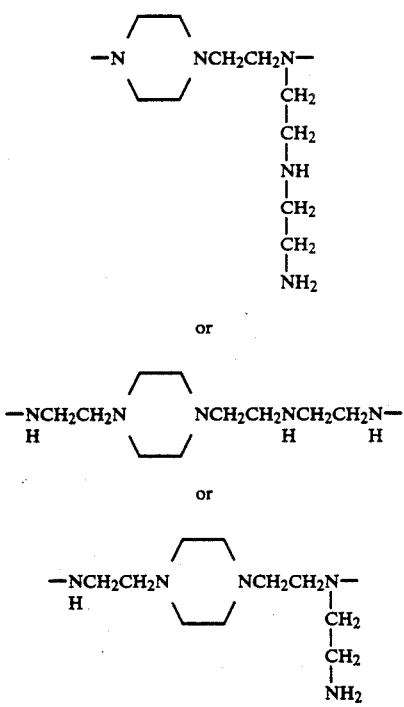

As shown from the above structures, examples include propylene-linked polyethylene polyamines and propylene-linked polyethylene polyamines with aminopropylated polyethylene polyamines. Specific examples include propylene-linked trietylenetetramine-tetraethylenepentamine; propylene-linked aminoethylpiperazine; propylene-linked diethylenetriamine-triethylenetetramine; propylene-linkd tetraethylenepentamine; propylene-linked aminoethylpiperazine-triethylenetetriamine; propylene-linked aminoethylpiperazine-tetraethylienepentamine; propylene-linked diethylenetriamine-amino-propylated triethylenetetramine; propylene-linked triethylenetetramine; propylene-linked diethylenetriamine and the like.

The propylene-linked polyethylene amines are prepared by the cyanoethylation of polyamines containing an ethylene linkage, e.g., those having from 1-6 ethylene groups such as diethylenetriamine, triethylenetetramine, and aminoethylpiperazine and then effecting reductive alkylation of the resulting cyanoethylated polyethylene polyamine in the presence of hydrogen. In this process cyanoethylation is accomplished by conventional reaction of the polyethylene polyamine with acrylonitrile or methacrylonitrile. Typically, acrylonitrile or methacrylonitrile are reacted with an ethylene radical containing polyamine in a mole ratio of 0.1 to 1.5 moles acrylonitrile per mole of polyamine containing the ethylene linkage, e.g., polyethylene polyamines. Preferably from about 0.5 to 1.0 moles acrylonitrile are reacted with per mole of polyethylene polyamine, e.g., diethylenetriamine (DETA) or triethylenetetramine (TETA). This reaction is carried out usually at a temperature of from 0 to 100° C., at pressures from about 1 to 20 psig. A reaction time from about 0.5 to 2 hours is generally required for the cyanoethylation.

The key to forming the propylene-linked polyethylene polyamine is the catalytic hydrogenation of the cyanoethylated polyamine. The key is carrying out the hydrogenation under conditions such that reductive alkylation occurs. When reductive alkylation occurs the nitrile providing molecule reacts with the amine providing molecule liberating ammonia and, the resulting polyethylene polyamines are linked via a propylene bridging group. This is in contrast to prior art processes where the catalytic hydrogenation is carried out under nonreductive alkylation conditions. In that case, the cyano group is hydrogenated to the primary amine to form an amino propylated polyethylene polyamine or reformed with other polyamines as opposed to undergoing reductive alkylation. To effect reductive alkylation, the catalytic hydrogenation is carried out using a hydrogenation catalyst which is extremely reactive and capable of carrying out such reductive alkylations. From our experience, it has been found palladium, platinum or rhodium on alumina are the only catalysts which permit the reductive alkylation of the cyanoethylated polyethylene polyamine to form the propylene-linked polyethylene polyamines. Utilization of another hydrogenation catalyst such as Raney nickel, cobalt or rhodium on carbon typically results in the formation of aminopropylated polyethylene polyamines as opposed to the bridged propylene-linked polyethylene polyamines. The hydrogenation is carried out in the absence of ammonia which is usually accomplished by venting to enhance reductive alkylation and thereby minimize hydrogenation of the cyano group to the primary amine. The catalytic hydrogenation is carried out at a temperature ranging from 50 to 150° C. and hydrogen pressures of from 50 to 2000 psig. Higher pressures may be used but are not necessary.

The catalyst used for the catalytic hydrogenation is palladium on alumina and the metal content of palladium on alumina may range from 0.1 to 10% by weight. preferably from 2 to 6%. The amount of supported catalyst charged to the reactor is between 0.5 and 10%, preferably between 2 and 8% of the total charge. High amounts of catalyst do not substantially improve the rate of reaction. For the reductive alkylation reaction, the ratio of polyethyleneamine to cyanoethylated polyamine may range from 0 to 3 or more. The preferred ratio is from 1 to 2. At 0, a larger amount of multi-propylene-linked polyethyleneamines are produced while at the higher ratios, predominantly polyethylene molecules linked with a single propylene group are formed. Ratios higher than 3 only serve to increase the amount of unreacted polyethyleneamine that will eventually have to be recycled.

Subsequent to the catalytic hydrogenation of the cyanoalkylated polyethylene polyamine, the product propylene-linked polyethylene polyamine is recovered from the reaction mixture. Typically, the reaction mixture will contain various polyethylene polyamines including modest levels of aminopropylated polyamine and other derivatives. Recovery of the propylene-linked polyethylene polyamines can be achieved by removing unreacted polyethyleneamine and aminopropylated polyethyleneamine by distillation at pressures ranging from 1 to 500 torr. The lower boiling components may be recycled.

The following examples are provided to illustrate various embodiments of the invention and are not intended to restrict the scope thereof.

EXAMPLE 1

Cyanoethylation of DETA (CNDETA)

In a 250 ml three necked round bottomed flask equipped with a magnetic stirring bar, thermometer, condenser and addition funnel was charged 51.0g (0.5 mole) DETA. Acrylonitrile, 26.5g (0.5 mole), was added dropwise from the funnel and at such a rate to maintain the temperature at 50±5° C. The addition took about 30 min. After the addition the mixture was stirred for an additional 20 minutes. The product had the following composition (area %) as determined by g.c. analysis (Table I).

TABLE I

| CYANOETHYLATION OF DETA | |
|---|---|
| COMPONENT[a] | AREA %[b] |
| DETA - diethylenetriamine | 20.68 |
| N'-CYANOETHYLDETA (N'-CEDETA) | 1.76 |
| N-CYANOETHYLDETA (N-CEDETA) | 49.54 |
| N,N'-DICYANOETHYLDETA (N,N'-DCEDETA) | 2.05 |
| N,N-DICYANOETHYLDETA (N,N-DCEDETA) | .53 |
| N,N''-DICYANOETHYLDETA (N,N''-DCEDETA) | 22.10 |
| N,N', N''-TRICYANOETHYLDETA (N,N',N''-TCEDETA) | .84 |
| N,N,N''-TRICYANOETHYLDETA (N,N,N''-TCEDETA) | .42 |
| OTHERS | 1.63 |
| | 100.00 |

[a]Assignments made by GC-MS,
$$\text{NH}_2\text{CH}_2\text{CH}_2\overset{H}{N}\text{CH}_2\text{CH}_2\overset{N'}{N}\text{H}\text{CH}_2\text{CH}_2\overset{N''}{N}\text{H}_2 \text{ (DETA)}$$
—CH$_2$CH$_2$CN (CYANOETHYL GROUP)
[b]Chromatography was conducted on a capillary DB-5 column.

EXAMPLE 2

Preparation of Propylene-linked Diethylenetriamine - PL-DETA

A 1 liter stirred autoclave was charged with 600g of cyanoethylated DETA having a composition similar to that shown in Table I and 32.0g of 5% Pd on alumina. After purging with nitrogen followed by hydrogen, the temperature was raised to 125° C. and the hydrogen pressure raised to 530 psig and maintained there for 24 hours while stirring at 400 rpm. The catalyst was removed by filtration. This procedure was repeated five times.

A portion of the filtered crude product, 1525g, with a color of 1 on the Gardner scale was distilled at 2–2.5 torr in a simple still. The vapor temperature was 100–105° C. while the pot temperature rose from 130 to 135° C. during the distillation. The distillate weighed 660g and the product (distillation residue) 860g. Five g was lost in handling.

The composition (area %) of distillate was 61.1% DETA and 30% mono aminopropylated DETAs. The remaining components were not identified. The residue was 4.5% Composition I and 54.6% Composition II, the propylene-linked DETAs as identified by gc-ms. The remainder was composed of 16.9% of lower retention time components and 24.0%, of higher retention time components.

Table II lists some chemical and physical properties of the product.

Composition I

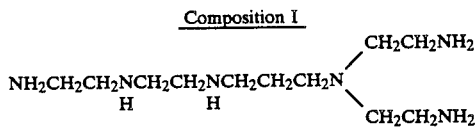

Composition II

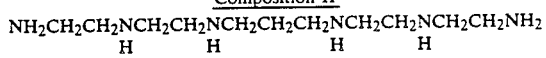

TABLE II

| PROPERTIES OF PROPYLENE-LINKED DETA | |
|---|---|
| Total Amine[a] | 22.1 meq/g |
| Primary Amine[b] | 6.17 meq/g |
| Secondary Amine[c] | 14.4 meq/g |
| Tertiary Amine[d] | 1.53 meq/g |
| Color[e] | 2 |
| Ave. Mole Wt.[f] | 349 g/mole |
| Viscosity @ 25° C.[g] | 167 cs |
| Wt. % Nitrogen[h] | 31.0% |

[a]Total milliequivalents of basic nitrogen per gram of product as determined by elements analysis.
[b]Milliequivalents of primary amine functionality per gram of product as determined by standard 2,5-pentanedione test for primary amine.*
[c]Calculated as the difference of the total amine less primary amine and tertiary amine.
[d]Milliequivalents of tertiary amine per gram of product as determined by acid titration after acetylation of primary and secondary amine with acetic anhydride.*
[e]Gardner scale, ASTM D-1544.
[f]Determined by GPC on Ultrastyrage ® columns.
[g]Determined on a Brookfield viscometer.
[h]Determined by microcombustion.
*S. Siggia, Quantitative Organic Analysis via Functional Groups, 4th ed., p. 594, 621.

EXAMPLE 3

Cyanoethylation of TETA

A commercial triethylenetetramine (TETA), 216g (1.48 mole), and 20 ml of toluene were charged to a 1 liter round bottomed flask and cooled to 5° C with the aid of magnetic stirring. Acrylonitrile (ACN), 40g (0.75 mole), and 10ml toluene were added slowly from a dropping funnel at a rate which kept the temperature below 9° C. A sample was withdrawn and analyzed by gc. The analysis is shown in Table III. The toluene then was stripped off in 1.5 hours by rotary evaporation under water pump vacuum at 70° C.

TABLE III

| GC ANALYSIS OF CYANOETHYLATED TETA | |
|---|---|
| COMPONENT | AREA % |
| TOLUENE | 4.00 |
| TAEA[1] | 4.07 |
| TETA[2] | 28.63 |
| BAEP[3] | 8.52 |
| PEEDA[4] | 3.32 |
| CETAEA[5] | 7.15 |
| N'-CETETA[6] | 1.46 |
| N-CETETA[7] | 23.45 |
| CEBAEP[8] | 4.99 |

TABLE III-continued

GC ANALYSIS OF CYANOETHYLATED TETA

| COMPONENT | AREA % |
|---|---|
| CEPEEDA[9] | 6.57 |
| DCETETA$_1$[10] | 1.60 |
| DCETETA$_2$[10] | 2.47 |
| DCEBAEP[11] | 0.49 |
| DCEPEEDA[12] | 1.34 |
| OTHERS | 1.94 |

[1]TAEA = tri(2-aminoethyl)amine
[2]TETA = linear triethylenetetramine
[3]BAEP = bis-aminoethylpiperazine
[4]PEEDA = piperazinoethylethylenediamine
[5]CETAEA = cyanoethyl-tri(aminoethyl)amine
[6]N'-CETETA = cyanoethyl-triethylenetetramine $$NH_2CH_2CH_2N\begin{matrix}CH_2CH_2CN\\ \\CH_2CH_2NHCH_2CH_2NH_2\end{matrix}$$

[7]N-CETETA = cyanoethyl-triethylenetetramine
$NH_2CH_2CH_2NHCH_2CH_2NHCH_2CH_2NHCH_2CH_2CN$
[8]CEBAEP = cyanoethyl-bis-aminoethylpiperazine
[9]CEPEEDA = cyanoethylpiperazinoethylethylenediamine
[10]DCETETA = dicyanoethyltriethylenetetramine, subscripts refer to different isomers
[11]DCEBAEP = dicyanoethyl-bis-aminoethylpiperazine
[12]DCEPEEDA = dicyanoethylpiperazinoethylethylenediamine

EXAMPLE 4

Hydrogenation of Cyanoethylated TETA (CETETA) with Palladium on Alumina

A 1 liter stirred autoclave was charged with 32.0g 5% palladium on alumina (Engelhard Cat. #2223001) and 600g of a mixture of TETAs and CETETAs (see Table IV) prepared by reacting 1 part by wt. acrylonitrile with 5.508 parts by wt. commercial TETA at ≦40° C. After sweeping air from the autoclave with N2 followed by H2, the temperature was increased to 125° C. and the hydrogen pressure to 530 psig. The reaction was run for 23 hours with stirring at 400 rpm before cooling, discharging and filtering out the catalyst. The reaction was repeated again. A 1053.6g portion of the filtered crude product was distilled under vacuum (2-2.5 torr) to remove the unreacted TETA's and aminopropylated TETA's. The distillate (bp 135-145° C./2-2.5) weighed 540.5g while the product remaining as a still residue weighed 510.0g and only 3.1 g was lost through handling. The distillate contained (area %) 69.6% TETAs and 30.4% aminopropylated TETAs. The residue contained 8.1% TETAs, 29.3% aminopropylated TETAs and 62.6% propylene-linked TETAs. These figures are gc area % and are not to be confused with wt% since the detector response of the long retention time components, i.e., the PLTETAs, is quite low and consequently the weight percent is significantly higher than the area percent reported. The two largest components were compositions III and IV and they accounted for 11.8% and 27.6%, resp., of the PLTETA portion of the product.

Table V lists some chemical and physical properties of the feedstock and distillation residue.

Composition III

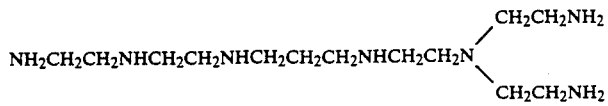

$$NH_2CH_2CH_2NHCH_2CH_2NHCH_2CH_2CH_2NHCH_2CH_2N\begin{matrix}CH_2CH_2NH_2\\ \\CH_2CH_2NH_2\end{matrix}$$

Composition IV

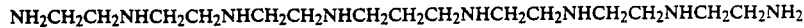

$NH_2CH_2CH_2NHCH_2CH_2NHCH_2CH_2NHCH_2CH_2CH_2NHCH_2CH_2NHCH_2CH_2NH_2$

TABLE IV

GC ANALYSIS OF CYANOETHYLATED TETA FEEDSTOCK

| COMPONENT | AREA % |
|---|---|
| TAEA[1] | 4.63 |
| TETA[2] | 24.68 |
| BAEP[3] | 11.57 |
| PEEDA[4] | 5.36 |
| CETAEA[5] | 7.23 |
| N'-CETETA[6] | 1.56 |
| N-CETETA[7] | 18.63 |
| CEBAEP[8] | 6.24 |
| CEPEEDA[9] | 9.91 |
| DCETETA[10] | 2.67 |
| DCETETA[10] | 2.18 |
| DCEBAEP[11] | .99 |
| DCEPEEDA[12] | 2.18 |
| OTHERS | 2.17 |

[1]TAEA = tri(2-aminoethyl)amine
[2]TETA = linear triethylenetetramine
[3]BAEP = bis-aminoethylpiperazine
[4]PEEDA = piperazinoethylethylenediamine
[5]CETAEA = cyanoethyltri(aminoethyl)amine
[6]N'-CETETA = cyanoethyltriethylenetetramine $$NH_2CH_2CH_2N\begin{matrix}CH_2CH_2CN\\ \\CH_2CH_2NHCH_2CH_2NH_2\end{matrix}$$

[7]N-CETETA = cyanoethyltriethylenetetramine
$NH_2CH_2CH_2NHCH_2CH_2NHCH_2CH_2NHCH_2CH_2CN$
[8]CEBAEP = cyanoethylbisaminoethylpiperazine
[9]CEPEEDA = cyanoethylpiperazinoethylethylenediamine
[10]DCETETA = dicyanoethyltriethylenetetramine, subscripts refer to different isomers
[11]DCEBAEP = dicyanoethylbisaminoethylpiperazine
[12]DCEPEEDA = dicyanoethylpiperazinoethylethylenediamine

TABLE V

PROPERTIES OF PROPYLENE-LINKED TETA

| TOTAL AMINE[a] | 21.7 meq/g |
|---|---|
| PRIMARY AMINE[b] | 5.9 meq/g |
| SECONDARY AMINE[c] | 11.3 meq/g |
| TERTIARY AMINE[d] | 4.5 meq/g |
| COLOR[e] | 7 |
| AVE. MOLE WT.[f] | 358 |
| VISCOSITY @ 25° C.[g] | 612 |
| WT. % NITROGEN[h] | 30.4% |

[a]Total milliequivalents of basic nitrogen per gram of product as determined by elemental analysis.
[b]Milliequivalents of primary amine functionality per gram of product as determined by standard 2,5-pentanedione test for primary amine.*
[c]Calculated as the difference of the total amine less primary amine and tertiary amine.
[d]Milliequivalents of tertiary amine per gram of product as determined by acid titration after acetylation of primary and secondary amine with acetic anhydride.*
[e]Gardner scale, ASTM D-1544.
[f]Determined by GPC on Ultrastyragel ® columns.
[g]Determined on a Brookfield viscometer.
[h]Determined by microcombustion.
*S. Siggia, Quantitative Organic Analysis via Functional Groups, 4th ed., p. 594, 621.

EXAMPLE 5

Hydrogenation of Cyanoethyl AEP (CEAEP) over Palladium on Alumina

The hydrogenation was run in a manner similar to that in Example 4 but 600g of crude (undistilled) cyanoethylaminoethylpiperazine (CEAEP) was substituted for crude CETETA. The crude CEAEP contained (area %) 46.6% AEP, 48.2% ring nitrogen cyanoethyl AEP ($N_R$-CEAEP), 1.1% side chain cyanoethyl AEP (NS-CEAEP) and 1.2% dicyanoethyl AEP (DCEAEP) and was prepared from two molar equivalents of AEP and one of acrylonitrile. The hydrogenation was run for 22 hours before cooling, discharging and filtering out catalyst. The procedure was repeated and 1190g of the filtered crude was distilled under vacuum (2-2.5 torr). The distillate (bp 110-125° C.) weighed 530g and had three major components, AEP (78.3%) and two aminopropyl AEPs (13.4% and 5.9%). The distillation residue, 655g, was composed of three major components, Compositions V, VI and VII which were identified by gc-ms.

COMPOSITION V

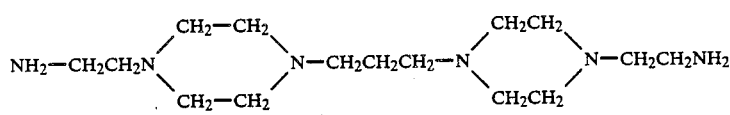

COMPOSITION VI

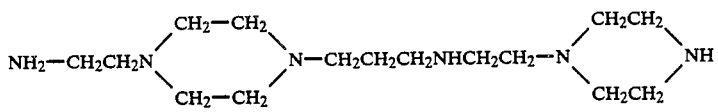

COMPOSITION VII

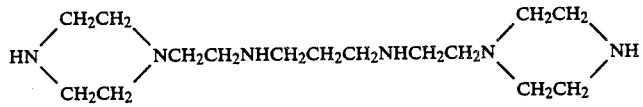

The composition of the PLAEP was 38.6% V, 47.7% VI and 2.5% VII (area %). The remainder (11.2%) was primarily higher molecular weight material.

Table VI lists some physical and chemical properties of the PLAEP mixture.

TABLE VI

| PROPERTIES OF PLAEP | |
|---|---|
| TOTAL AMINE[a] | 19.3 meq/g |
| PRIMARY AMINE[b] | 4.5 meq/g |
| SECONDARY AMINE[c] | 5.2 meq/g |
| TERTIARY AMINE[d] | 9.6 meq/g |
| COLOR[e] | 2 |
| AVE. MOLE WT.[f] | 335 g/mole |
| VISCOSITY[g] | 1600 cs |
| WT. % NITROGEN[h] | 27.1% |

[a]Total milliequivalents of basic nitrogen per gram of product as determined by elemental analysis.
[b]Milliequivalents of primary amine functionality per gram of product as determined by standard 2,5-pentanedione test for primary amine.*
[c]Calculated as the difference of the total amine less primary amine and tertiary amine.
[d]Milliequivalents of tertiary amine per gram of product as determined by acid titration after acetylation of primary and secondary amine with acetic anhydride.*
[e]Gardner scale, ASTM D-1544.
[f]Determined by GPC on Ultrastyragel ® columns.
[g]Determined on a Brookfield viscometer.
[h]Determined by microcombustion.
*S. Siggia, Quantitative Organic Analysis via Functional Groups, 4th ed., p. 594, 621.

EXAMPLE 6

Hydrogenation of Cyanoethyl AEP (CEAEP) over Rhodium on Alumina

A 100 ml stirred autoclave was charged with 5% rhodium on alumina (1.60g) and crude cyanoethylated AEP (CEAEP) (29.79g) prepared from 1 molar equivalent of acrylonitrile and 2 molar equivalents of aminoethylpiperazine. The CEAEP had the following composition (area %); AEP (47.0), $N_R$-CEAEP (48.5), $N_S$CEAEP (1.2), DCEAEP (0.6) and others (2.7). After purging air from the autoclave with nitrogen and then with hydrogen the temperature was raised to 126° C., the pressure to 500 psig and maintained at these conditions for 30 min. while stirring. The temperature was then decreased to 100° C. and maintained at 100° for 14.75 hrs. Essentially all hydrogen uptake occurred in the first 30 min. The product was analyzed by gc and contained the following components (area %); AEP (45.4), 4-(3-aminopropyl)-1-(2-aminoethyl)piperazine (22.7%), N-(3-aminopropyl)-2-(piperazino)ethylamine (1.1%), Composition V (1.2%), Composition VI (13.5%), Composition VII (0.6%) (for structures V, VI and VII see Example 5), Composition VIII (9.5%) (structure below) and others (6.0%).

Composition VIII

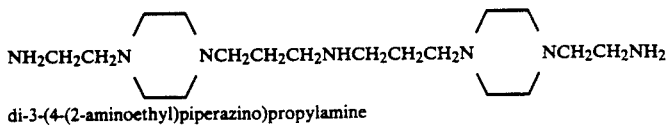

di-3-(4-(2-aminoethyl)piperazino)propylamine

Thus rhodium on alumina is also a catalyst which produces propylene-linked polyamines and di-propyleneamino-linked polyamines as is demonstrated by the unexpected high selectivity for Composition VIII, i.e., di-3-(4-(2-aminoethyl)piperazino)propylamine.

Table VII compares the properties of the propylene-linked polyamines, PL-DETA, PL-AEP, PL-TAEA and PL-TETA with commercially available polyamines, TETA, TEPA and a highers product from Dow Chemical Co. (E-100). Note the percent of primary, secondary and tertiary amine vary little from one commercial product to the next while the examples of the instant invention produces products which have as little as 23.4% primary to as much as 43.4% while secondary amine content varied from 26.8 to 65.2% and tertiary from 6.9 to 49.8%. This flexibility of structure was demonstrated for molecules with average molecular weights in the 350g/mole region while the highest ave. molecule weight of commercial polyamine is on the order of 250g/mole. Further, PLPs with the exception of PL-AEP have total amine values of the same order of magnitude as the commercially available higher polyamine, E-100.

AEP (4.8%), composition IX (2.5%), composition X (54.4%), composition V (2.0%) composition VI (2.5%), composition XI (1.7%) and others (13.7%) (see formula descriptions from Examples 5 and 6 and from structures following).

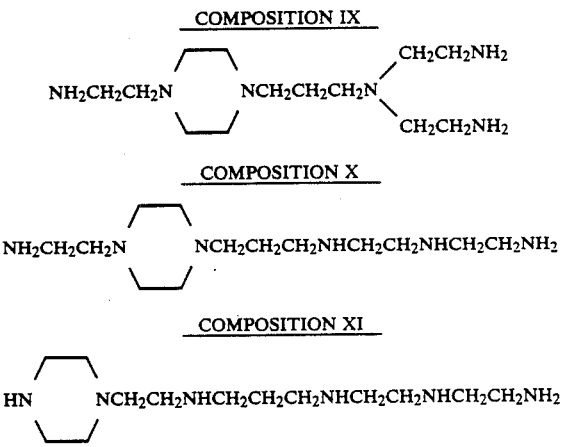

TABLE VII

| | COMPARISON OF PROPYLENE-LINKED POLYAMINE PROPERTIES WITH COMMERCIAL POLYAMINES | | | | | | |
|---|---|---|---|---|---|---|---|
| | PL-DETA | PL-AEP | PL-TAEA | PL-TETA | TETA | TEPA | HIGHERS[e] |
| Amine # (mg KOH/g) | 1240 | 1083 | 1264 | 1218 | 1423 | 1337 | 1203 |
| Primary (%) | 27.9 | 23.4 | 43.4 | 27.0 | 51.5 | 48.9 | 44.6 |
| Secondary (%) | 65.2 | 26.8 | 31.5 | 52.3 | 36.8 | 38.1 | 41.9 |
| Tertiary (%) | 6.9 | 49.8 | 25.1 | 20.7 | 11.7 | 13.0 | 13.5 |
| Color[f] | 2 | 2 | 5 | 7 | 1 | 3 | ~13 |
| Nitrogen (%) | 31.0 | 27.1 | 31.6 | 30.4 | 36.1 | 35.0 | 32.0 |
| Viscosity @ (centistokes) | 167 | 1600 | 465 | 612 | 24 | 88 | 125[a] |
| MW (AVE)[b] | 349 | 335 | 344 | 348 | 154[c] | 196[c] | 245[d] |

[a] @ 38° C.
[b] via GPC
[c] Calculated from GC data.
[d] Assumes average is pentaethylenehexamine (50% cyclic).
[e] Dow Chemical Co.'s, E-100 polyethyleneamine.
[f] Gardner scale

EXAMPLE 7

Hydrogenation of Cyanoethyl AEP in the Presence of DETA over Pd/Al[pb]2O3

A 100 ml stirred autoclave was charged with 1.60g 5% Pd on alumina (Engelhard Catalog #2223001), diethylenetriamine (DETA), 10.3g, and crude cyanoethylated AEP prepared by the addition of one mole of acrylonitrile to one mole of 1-(2-aminoethyl)piperazine (AEP). The crude cyanoethylated AEP was composed of (area %) AEP (1.9%), NR-CEAEP (85.2%), NS-CEAEP (10.1%) and others (2.8). The autoclave was heated to 125° C. after being purged air with nitrogen and then purged of nitrogen with hydrogen. The hydrogen pressure was raised to 500 psig and the reaction mixture stirred for 15 hours. A sample of the crude product was analyzed by gc and found to contain (area %) DETA (10.5%), AEP (7.7%), aminopropylated This experiment shows that mixed propylene-linked polyamines are readily formed by reacting hydrogen and a cyanoethylated polyamine with a second polyamine of a different structure over a palladium on alumina catalyst.

EXAMPLE 8

Epoxy Thermoset Resins Effect of Amine Curing Agents

Test epoxy thermoset resins were formed in a conventional manner using a commercial diglycidyl ether of bisphenyl A having an epoxide equivalent weight of 190 as the polyepoxide resin and stoichiometric amounts of test amine curing agents. The epoxide resins were cured with the amine to form an epoxy thermoset resin and the resulting epoxy thermoset resin tested for tensile strength and hardness. In addition, reactivity, exotherm and amine carbonate formation were measured. The utility of the propylene-linked technology in epoxy resin systems was shown by making a direct comparison of reactivity and cured properties for various ethyleneamines and the corresponding propylene-linked analogs. The products tested are listed below:

Diethylenetriamine (DETA) vs. PL-DETA
Triethylenetetramine (TETA) vs. PL-TETA
Aminoethylpiperazine (AEP) vs. PL-AEP
tris(aminoethyl) amine (TAEA) vs. PL-TAEA Table VIII sets forth the test procedure and results for the sample amine curing agents utilized.

TABLE VIII

Comparison of Properties
Propylene-Linked Amines vs. Polyethyleneamines

| | DETA | PL-DETA | TETA | PL-TETA | AEP | PL-AEP | TAEA | PL-TAEA |
|---|---|---|---|---|---|---|---|---|
| Tensile Strength (psi)[1] | 11260 | 10565 | 10430 | 11780 | 11380 | 10993 | 11780 | 10710 |
| Tensile Modulus ($10^5$ psi) | 2.8 | 2.6 | 2.6 | 2.8 | 2.8 | 3.0 | 3.0 | 2.7 |
| Tensile Elongation at Break (%) | 7.2 | 8.3 | 7.9 | 8.4 | 7.5 | 7.1 | 7.6 | 7.6 |
| Gel Time (minutes)[2] | 33 | 30 | 33 | 40 | 17 | 62 | 35 | 55 |
| Peak Exotherm (°C.)[2] | 301 | 267 | 250 | 193 | 313 | 219 | 287 | 147 |
| Shore D Hardness[3] | 81 | 81 | 83 | 81 | 79 | 82 | 78 | 70 |
| Amine Carbonate Formulation | | | | | | | | |
| ¼"Selection[3] | Moderate | Slight | Moderate | Slight | Very Slight | None | Very Slight | None |
| 5 Mil Film, 100% RH | Severe | Severe | Severe | Severe | Severe | Moderate | Severe | Severe |

[1]Tensile properties were determined using ¼" thick castings cured overnight at 23° C. then two hours at 100° C. DER 331 (EEW = 190) was cured with a stoichiometric amount of amine in each case.
[2]Gel time and peak exotherm were measured using a 100 g mass. Individual components were equilibrated at 23° C. for 24 hours prior to mixing.
[3]Shore D Hardness specimens were prepared by casting a ¼" thick section in a quart paint can lid. Cure was for 7 days at 23° C. These samples were also used for the amine carbonate formation testing.
[4]Drawdowns on aluminum panels were suspended above water in a covered container and allowed to cure overnight at 23° C.

and 10ml toluene were added slowly from a dropping funnel at a rate which

The above results show that polyethyleneamines, such as DETA, TETA and AEP, which are the building blocks for most of the aliphatic amine-based curing agents for epoxy resins have many good features, they have disadvantages such as high vapor pressure, inconvenient combining ratio, difficult mixing, short pot life, high exotherm and amine carbonate formation. The propylene-linked polyethyleneamines offer an ability to eliminate some of the disadvantages associated with standard ethyleneamines. Advantages for these materials include low vapor pressure, lower primary amine content, higher secondary amine content and higher molecular weight.

The following general trends also were evident for the propylene-linked amines relative to the unlinked precursor:

1. More convenient combining ratio
2. Easier mixing
3. Longer pot-life
4. Lower exotherm
5. Less amine carbonate formation
6. Equivalent strength
7. Equivalent flexibility The propylene-linked amines offered measurable improvements in performance relative to the polyethylene amines.

What is claimed is:

1. In a catalytic process for the hydrogenation of a cyanoethylated polyamine containing an ethylene linkage, wherein said polyamine containing the ethylene linkage is contacted with a hydrogenation catalyst in the presence of hydrogen under hydrogenation conditions, the improvement for producing a propylene-linked polyamine containing an ethylene linkage which comprises carrying out the hydrogenation of the cyanoethylated polyamine containing an ethylene group in the presence of a hydrogenation catalyst selected from the group consisting of palladium, platinum and rhodium which contains from about 2-6 active metal by way of the catalyst including support, at a temperature of from 50–150° C., a pressure of 50–2000 psig and for a time for effecting reductive alkylation.

2. The process of claim 1 wherein the catalyst is present in an amount from about 0.5 to 10% by weight of the cyanoethylated polyamine containing an ethylene linkage and polyethylene polyamine containing an ethylene linkage is present.

3. The process of claim 2 wherein the hydrogenation catalyst is palladium or rhodium supported on alumina.

4. The process of claim 3 wherein at least a portion of the cyanoethylated polyethyleneamine is diethylenetriamine and the polyethylene polyamine is diethylenetriamine, triethylenetetramine, tetraethylenepentamine or aminoethylpiperazine.

5. The process of claim 3 wherein at least a portion of the cyanoethylated polyethylene polyamine is triethylenetetramine and the polyethylene polyamine is diethylenetriamine, triethylenetetramine, tetraethylenepentamine or aminoethylpiperazine.

6. The process of claim 3 wherein at least a portion of the cyanoethylated polyethylenepolyamine is a tetraethylenepentamine and the polyethylene polyamine is diethylenetriamine, triethylenetetramine, tetraethylenepentamine or aminoethylpiperazine.

7. The process of claim 3 wherein the cyanoethylated polyethylene polyamine is cyanoethylated aminoethylpiperazine and the polyethylene polyamine is aminoethylpiperazine.

* * * * *